United States Patent [19]
Leschinsky et al.

[11] Patent Number: 5,817,001
[45] Date of Patent: Oct. 6, 1998

[54] METHOD AND APPARATUS FOR DRIVING AN INTRA-AORTIC BALLOON PUMP

[75] Inventors: Boris Leschinsky, Waldwick; Jonathan R. Williams, Montville, both of N.J.

[73] Assignee: Datascope Investment Corp., Montvale, N.J.

[21] Appl. No.: 863,232

[22] Filed: May 27, 1997

[51] Int. Cl.⁶ .................................................. A61M 1/10
[52] U.S. Cl. ................................................................ 600/18
[58] Field of Search ........................... 600/18, 495–496; 606/201–203, 192–195; 623/3, 26

[56] References Cited

U.S. PATENT DOCUMENTS

| | | |
|---|---|---|
| 3,550,582 | 12/1970 | Wilhelmson ............................ 600/496 |
| 3,585,983 | 6/1971 | Kantrowitz et al. . |
| 3,818,903 | 6/1974 | Bleecker . |
| 4,135,496 | 1/1979 | Chazov et al. ............................... 523/3 |
| 4,546,760 | 10/1985 | Suzuki et al. . |
| 4,548,550 | 10/1985 | Tsuji . |
| 4,556,997 | 12/1985 | Takamiya et al. . |
| 4,648,385 | 3/1987 | Oumi et al. . |
| 4,662,829 | 5/1987 | Nehring . |
| 4,692,148 | 9/1987 | Kantrowitz et al. . |
| 4,787,368 | 11/1988 | Kageyama . |
| 4,794,910 | 1/1989 | Mushika . |
| 4,796,606 | 1/1989 | Mushika . |
| 4,832,005 | 5/1989 | Takamiya et al. . |
| 4,942,735 | 7/1990 | Mushika et al. . |
| 4,969,866 | 11/1990 | Inagaki . |
| 4,974,774 | 12/1990 | Nakagawa et al. . |
| 5,062,775 | 11/1991 | Orth . |
| 5,064,353 | 11/1991 | Tsukahara . |
| 5,100,374 | 3/1992 | Kageyama . |
| 5,147,392 | 9/1992 | Inagaki et al. . |
| 5,158,529 | 10/1992 | Kanai . |
| 5,169,379 | 12/1992 | Freed et al. . |
| 5,217,430 | 6/1993 | Mushika . |

*Primary Examiner*—William E. Kamm
*Attorney, Agent, or Firm*—Lerner, David, Littenberg, Krumholz & Mentlik

[57] ABSTRACT

An intra-aortic balloon pump includes an overdrive system for inflating the intra-aortic balloon with a working gas and deflating the balloon more rapidly. A substantially constant inflation pressure is applied to the working gas for a predetermined time to substantially fully inflate the balloon to a working pressure. The inflation pressure is then reduced to a pressure which is substantially equal to the working pressure so as to maintain the balloon in the inflated condition and prevent its overinflation. Subsequently, a substantially constant deflation pressure is applied to the working gas and is held for a predetermined time to substantially fully deflate the balloon to a desired end deflation pressure. The deflation pressure is then increased to a pressure which is substantially equal to the end deflation pressure so as to maintain the balloon in the deflated condition and ready the system for the next inflation cycle.

40 Claims, 8 Drawing Sheets

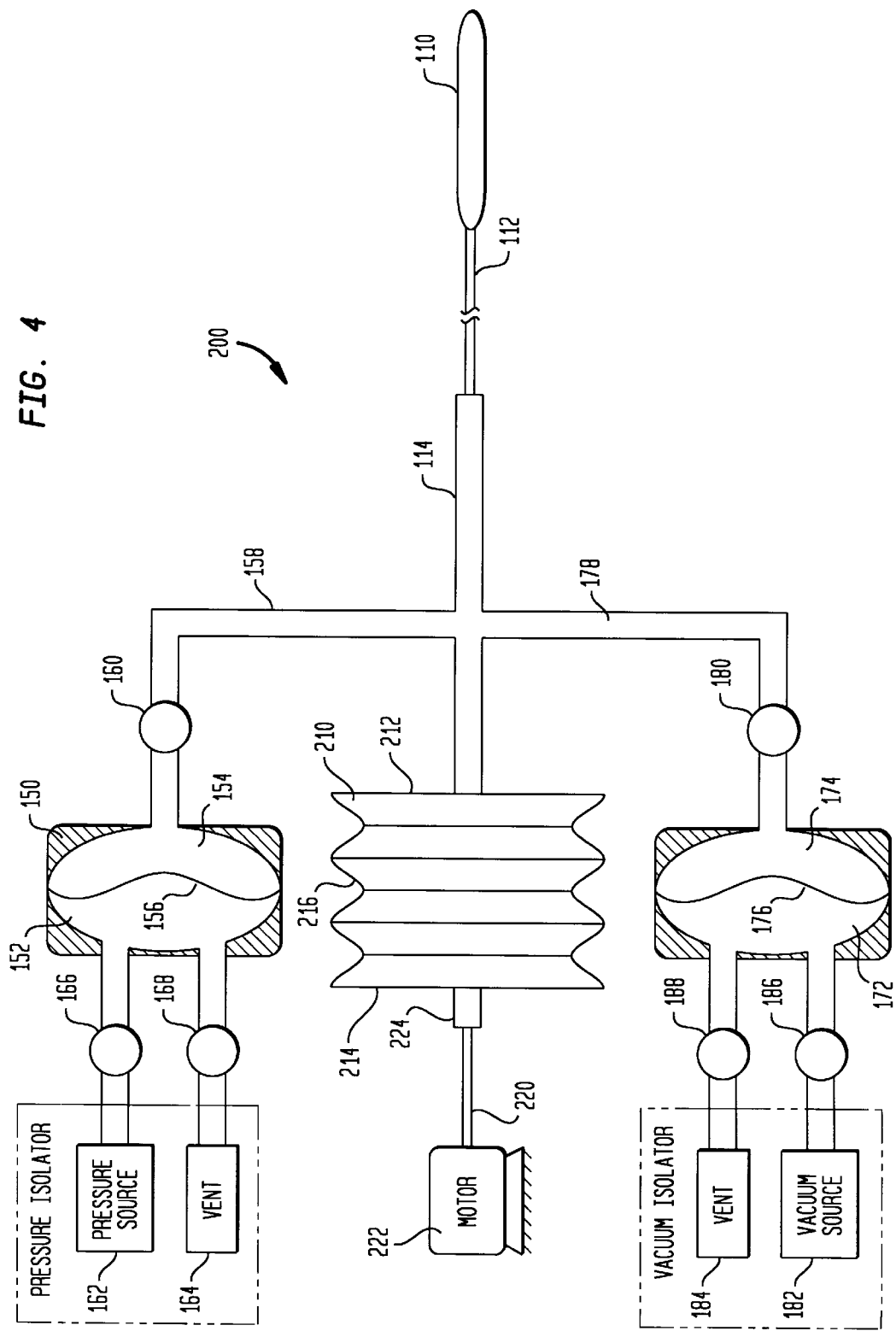

METHOD AND APPARATUS FOR DRIVING AN INTRA-AORTIC BALLOON PUMP

FIELD OF THE INVENTION

The present invention relates generally to intra-aortic balloon pumps, and more particularly, to systems for inflating and deflating intra-aortic balloons. Still more particularly, the present invention relates to such a system incorporating an overdrive component for inflating and deflating the intra-aortic balloon more rapidly.

BACKGROUND OF THE INVENTION

Intra-aortic balloon pump therapy is frequently prescribed for patients who have suffered a heart attack or some other form of heart failure. In such therapy, a thin balloon is inserted through an artery into the patient's aorta. The balloon is connected through a series of thin tubes to a complex apparatus which causes the balloon to inflate and deflate repeatedly in time with the patient's heart beat, thereby assuming some of the load of the heart during the patient's recovery period.

The inflation/deflation apparatus supplies positive pressure for expanding the balloon during an inflation cycle and negative pressure for contracting the balloon during a deflation cycle. In a conventional prior art apparatus, shown schematically in FIG. 1, an intra-aortic balloon 10 is surgically inserted into a patient's aorta and is connected through a thin catheter 12 and a larger diameter extender 14 to an isolator 18 divided by a pliant membrane 20 into a primary side 22 and a secondary side 24. The entire volume between membrane 20 and balloon 10 is typically filled with a gas, such as helium, supplied by a gas source 26. A positive pressure source 28 is connected through a solenoid valve 30 to the input or primary side 22 of isolator 18. Similarly, a negative pressure source 32 is connected through a solenoid valve 34 to the input or primary side 22 of isolator 18. The primary side 22 of isolator 18 is also connected through a solenoid valve 36 to a vent or exhaust port 38.

During an inflation cycle, solenoid valve 30 is opened to permit positive pressure from positive pressure source 28 to enter primary side 22 of isolator 18. This positive pressure causes membrane 20 to move toward secondary side 24, thereby forcing the helium in the secondary side to travel toward and inflate balloon 10. For deflation, solenoid valve 30 is closed and solenoid valve 36 is opened briefly to vent the gas from primary side 22, after which valve 36 is closed. Solenoid valve 34 is then opened, whereupon negative pressure source 32 creates a negative pressure on the primary side 22 of isolator 18. This negative pressure pulls membrane 20 toward primary side 22, whereby the helium is drawn out from the balloon.

It is desirable in intra-aortic balloon pump therapy to inflate and deflate the balloon as rapidly as possible. Rapid cycling would permit the therapy to be performed more effectively, and would enable smaller diameter catheters to be used, thereby reducing the possibility of limb ischemia. Although the prior art system described above permits rapid inflation and deflation cycles, the configuration of this system creates inherent limitations in the cycle speed which can be achieved.

Thus, in a typical inflation cycle, pressurized gas from positive pressure source 28, at an initial pressure of about 8 psi, is used to inflate balloon 10 to an end inflation pressure of about 2 psi, which is about the blood pressure of a normal patient. (In the present specification, all references to psi, unless otherwise noted, are to gauge pressures, not absolute pressures.) In the initial portion of the inflation cycle, the 8 psi gas pressure on the primary side 22 of isolator 18 drives membrane 20 toward the secondary side 24, forcing the gas in secondary side 24 into extender 14. Because of its small diameter, however, catheter 12 acts as a constriction to the rapid flow of gas to balloon 10. Hence, when membrane 20 has moved fully forward (i.e., it hits the wall on secondary side 24), there is a relatively large pressure differential across catheter 12, and balloon 10 is only partially inflated. The process of balloon inflation continues as the gas in extender 14 flows through catheter 12 to the balloon until a state of equilibrium is reached in the closed portion of the system. It is therefore apparent that the pressure differential across catheter 12 is highest at the beginning of the inflation cycle and drops to zero at the end of the inflation cycle. Since the rate at which gas flows from extender 14 to balloon 10 is dependent upon the pressure differential across catheter 12, this gradual decay in the pressure differential results in a steadily decreasing flow rate and, therefore, a longer overall time until equilibrium is reached and the balloon is fully inflated.

A similar situation occurs during the deflation portion of the cycle. Thus, as the deflation cycle begins, a large negative pressure is created on primary side 22 of isolator 18 by negative pressure source 32. This negative pressure pulls membrane 20 toward primary side 22, whereupon the gas in extender 14 is drawn into the secondary side 24 of the isolator. Again, the small diameter of catheter 12 constricts the flow of gas out from balloon 10 such that, with membrane 20 moved to its fully retracted position (i.e., against the wall on primary side 22), a relatively large pressure differential exists across catheter 12, and balloon 10 is only partially deflated. As helium flows slowly from balloon 10 through catheter 12, the balloon continues to deflate until equilibrium is reached. Here again, the pressure differential across catheter 12 which drives balloon deflation is at its highest at the beginning of the deflation cycle and drops to zero at the end of the cycle. The gradual decrease in the pressure differential results in a steadily decreasing flow rate across catheter 12, lengthening the overall time until the balloon is fully deflated.

At first blush, it would appear that faster inflation/deflation speeds can be achieved simply by using a higher positive pressure during inflation and a lower negative pressure during deflation. The use of a higher positive pressure, however, creates the risk of overinflating and stressing the balloon, with the attendant risk of aneurization or rupturing of the balloon. Alternatively, simply increasing the volume of the isolator so that the maximum pressure differential across catheter 12 would be maintained for a longer period of time before membrane 20 has bottomed out would, without other modification to the system, create problems. Not only would there be a risk of damaging the balloon through overinflation, there would also be a need to remove a larger amount of gas from the balloon during deflation, which requirement would increase the deflation time.

There therefore exists the need for an improved system which will both inflate and deflate intra-aortic balloons more rapidly than is capable with conventional systems, but which will not require higher magnitude operating pressures and the risks of leakage and balloon failure attendant therewith.

SUMMARY OF THE INVENTION

The present invention addresses these needs.

One aspect of the present invention provides a method for inflating and deflating a medical device, the medical device being connected to a conduit having a first end connected to the medical device and a second end, the medical device and the conduit being filled with a working gas. In accordance with the method, a first positive pressure is applied to the working gas at the second end of the conduit and is maintained for a predetermined time to substantially fully inflate the medical device to a working pressure lower than the first positive pressure. The pressure at the second end of the conduit is then reduced to a second positive pressure substantially equal to the working pressure, and thereafter is reduced to a third pressure lower than the second positive pressure to deflate the medical device.

In accordance with one embodiment of the method of the present invention, the first positive pressure is applied from first and second sources connected in parallel with one another. In accordance with this embodiment, application of the first positive pressure may include the steps of moving a first amount of the working gas from the first source toward the second end of the conduit and moving a second amount of the working gas from the second source toward the second end of the conduit. Preferably, the second amount is less than the first amount. In preferred embodiments, the second source may include a chamber having a predetermined volume, and the step of moving the second amount of the working gas may include the step of moving a volume of the working gas substantially equal to the predetermined volume from the chamber toward the second end of the conduit.

In a variant of this embodiment, the pressure at the second end of the conduit may be reduced to the second positive pressure by moving a volume of the working gas substantially equal to the predetermined volume from the second end of the conduit into the chamber.

In accordance with another embodiment hereof, the first positive pressure may be applied by moving a first amount of the working gas to the second end of the conduit, and the pressure at the second end of the conduit may be reduced to the second positive pressure by removing a second amount of the working gas less than the first amount from the second end of the conduit. In accordance with this embodiment, the pressure at the second end of the conduit may be reduced to the third pressure by removing a third amount of the working gas from the second end of the conduit, the second amount and the third amount together being substantially equal to the first amount.

In yet another embodiment, the pressure at the second end of the conduit may be reduced to the third pressure by applying a first negative pressure to the working gas at the second end of the conduit, maintaining the first negative pressure for a predetermined time to substantially fully deflate the medical device to a deflation pressure higher than the first negative pressure, and increasing the pressure at the second end of the conduit to a second negative pressure substantially equal to the deflation pressure. In accordance with this embodiment, the first negative pressure may be applied from first and second sources connected in parallel with one another. In a preferred arrangement, application of the first negative pressure may include the steps of moving a first amount of the working gas from the second end of the conduit toward the first source and moving a second amount of the working gas from the second end of the conduit toward the second source. Preferably, the second amount is less than the first amount. Still more preferably, the second source may include a chamber having a predetermined volume, and the step of moving the second amount of the working gas may include the step of moving a volume of the working gas substantially equal to the predetermined volume from the second end of the conduit into the chamber.

In a variant of this last embodiment, the pressure at the second end of the conduit may be increased to the second negative pressure by moving a volume of the working gas substantially equal to the predetermined volume from the chamber toward the second end of the conduit.

In a further variant of this last embodiment, the first negative pressure may be applied by removing a first amount of the working gas from the second end of the conduit, and the pressure at the second end of the conduit may be increased to the second negative pressure by supplying an amount of the working gas less than the first amount to the second end of the conduit.

Another aspect of the present invention provides a method for inflating and deflating a medical device, the medical device being connected to a conduit having a first end connected to the medical device and a second end connected to an operating apparatus, the medical device, the conduit and the operating apparatus being filled with a working gas. In a method in accordance with this aspect of the invention, the operating apparatus is placed in an inflation condition to produce a pressure differential across the conduit with the pressure of the working gas in the operating apparatus at a first positive pressure and the pressure of the working gas in the medical device at a second positive pressure less than the first positive pressure, whereby the working gas flows from the operating apparatus to the medical device to inflate the medical device. The pressure differential across the conduit is maintained for a predetermined time to substantially fully inflate the medical device to a working pressure lower than the first positive pressure. The operating apparatus may then be placed in an intermediate condition to reduce the pressure of the working gas in the operating apparatus to a second positive pressure substantially equal to the working pressure, and thereafter may be placed in a deflation condition to reduce the pressure of the working gas in the operating apparatus to a third pressure lower than the second positive pressure, whereby gas flows from the medical device to the operating apparatus to inflate the medical device.

In one embodiment of the method in accordance with this aspect of the invention, the operating apparatus may be placed in the inflation condition by moving a first amount of the working gas from a first portion of the operating apparatus toward the second end of the conduit and moving a second amount of the working gas from an auxiliary portion of the operating apparatus toward the second end of the conduit. Preferably, the second amount is less than the first amount. In a variant of this method, the operating apparatus may be placed in the intermediate condition by reducing the pressure in the auxiliary portion to about the second positive pressure.

In another embodiment hereof, the operating apparatus may be placed in the deflation condition by placing the operating apparatus in a first deflation condition to produce a pressure differential across the conduit with the pressure of the working gas in the operating apparatus at a first negative pressure and the pressure of the working gas in the medical device at the working pressure, whereby the working gas flows from the medical device to the operating apparatus to deflate the medical device. The pressure differential across the conduit is maintained for a predetermined time to substantially fully deflate the medical device to a deflation pressure higher than the first negative pressure, and the operating apparatus is then placed in a second deflation condition to increase the pressure in the operating apparatus to a second negative pressure substantially equal to the deflation pressure.

A still further aspect of the present invention provides a medical apparatus including an inflatable member, a conduit having a first end connected to the inflatable member and a second end, a working gas contained within the inflatable member and the conduit, means for applying a first positive pressure to the working gas at the second end of the conduit, a control device for maintaining the first positive pressure for a predetermined time to substantially fully inflate the inflatable member to a working pressure lower than the first positive pressure, means for reducing the pressure at the second end of the conduit to a second positive pressure substantially equal to the working pressure, and means for reducing the pressure at the second end of the conduit to a third pressure lower than the second positive pressure to deflate the inflatable member.

In one embodiment of the apparatus of the present invention, the means for applying the first positive pressure may include a main positive pressure source and an auxiliary positive pressure source connected in parallel with one another. In accordance with this embodiment, the means for reducing the pressure at the second end of the conduit to the third pressure may include an auxiliary negative pressure source connected in parallel with the main positive pressure source.

In a preferred embodiment hereof, the main positive pressure source may include a main chamber and the auxiliary positive pressure source may include an auxiliary positive pressure chamber having a fixed volume. The main chamber desirably has a volume greater than the fixed volume. In a preferred arrangement, the means for reducing the pressure at the second end of the conduit to the second positive pressure may include the auxiliary positive pressure chamber. In a highly preferred arrangement, the means for reducing the pressure at the second end of the conduit to the third pressure may include a main negative pressure source including the main chamber.

In another embodiment of the medical apparatus, the means for reducing the pressure at the second end of the conduit to the third pressure may include a main negative pressure source and an auxiliary negative pressure source connected in parallel with one another. In accordance with this embodiment, the main negative pressure source may include a main chamber and the auxiliary negative pressure source may include an auxiliary negative pressure chamber having fixed volume. Desirably, the main chamber has a volume greater than the fixed volume.

In a still further embodiment, the means for reducing the pressure at the second end of the conduit to the third pressure may include means for applying a first negative pressure to the working gas at the second end of the conduit, a control mechanism for maintaining the first negative pressure for a predetermined time to substantially fully deflate the medical device to a deflation pressure higher than the first negative pressure, and means for increasing the pressure at the second end of the conduit to a second negative pressure substantially equal to the deflation pressure. In a preferred medical device in accordance with this embodiment, the means for applying the first negative pressure may include a main negative pressure source and an auxiliary negative pressure source connected in parallel with one another. The main negative pressure source may include a main chamber and the auxiliary negative source may include an auxiliary negative pressure chamber having a fixed volume. The main chamber desirably has a volume greater than the fixed volume. In a preferred arrangement, the means for increasing the pressure at the second end of the conduit to the second negative pressure may include the auxiliary negative pressure chamber.

In yet a further embodiment of the medical apparatus, the means for applying the first positive pressure may include a positive pressure source including a main chamber, and the means for reducing the pressure at the second end of the conduit to the second positive pressure may include an auxiliary chamber having a fixed volume connected in parallel with the main chamber.

In still another embodiment, the means for applying the first positive pressure may include a positive pressure source including a main chamber, and the means for reducing the pressure at the second end of the conduit to the second positive pressure may include an auxiliary chamber having a fixed volume connected in series with the main chamber.

Yet another aspect of the present invention provides a medical apparatus including an inflatable member having an inflated condition and a deflated condition, a working gas for inflating the inflatable member, a conduit having a first end connected to the inflatable member and a second end, a main pressure source for supplying a first amount of the working gas to the second end of the conduit and for removing the first amount of the working gas from the second end of the conduit, a positive pressure isolator connected in parallel with the main pressure source and having a primary side, a secondary side and a movable member separating the primary side from the secondary side, the secondary side being connected in flow communication with the second end of the conduit, a positive pressure source for supplying a positive pressure to the primary side of the positive pressure isolator to move the movable member toward the secondary side of the positive pressure isolator, thereby moving a second amount of the working gas from the secondary side of the positive pressure isolator to the second end of the conduit, and a controller for controlling the supply of positive pressure to the positive pressure isolator, whereby the inflatable member is placed in the inflated condition by supplying the first amount of the working gas from the main pressure source to the second end of the conduit together with movement of the second amount of the working gas from the secondary side of the positive pressure isolator to the second end of the conduit, and the inflatable member is placed in the deflated condition by removing the first amount of the working gas from the second end of the conduit.

In one embodiment of the medical apparatus in accordance with this aspect of the invention, the main pressure source may include a main isolator having a primary side, a secondary side and a movable member separating the primary side from the secondary side, the secondary side being connected in flow communication with the second end of the conduit, a main positive pressure source for supplying a positive pressure to the primary side of the main isolator to move the movable member toward the secondary side of the main isolator, thereby moving the first amount of the working gas to the second end of the conduit, and a main negative pressure source for supplying a negative pressure to the primary side of the main isolator to move the movable member toward the primary side of the main isolator, thereby moving the first amount of the working gas from the second end of the conduit to the secondary side of the negative pressure isolator.

In another embodiment hereof, the medical apparatus may further include a negative pressure isolator connected in parallel with the main pressure source and having a primary side, a secondary side and a movable member separating the primary side from the secondary side, the secondary side being connected in flow communication with the second end of the conduit, a negative pressure source for supplying a negative pressure to the primary side of the negative pressure isolator to move the movable member toward the primary side of the negative pressure isolator, thereby moving a third amount of the working gas from the second end of the conduit to the secondary side of the negative pressure isolator, and a controller for controlling the supply of negative pressure to the negative pressure isolator, whereby the inflatable member is placed in the deflated condition by removing the first amount of the working gas from the second end of the conduit to the main pressure source together with movement of the third amount of the working gas from the second end of the conduit to the secondary side of the negative pressure isolator.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 4 is a highly schematic view showing a variant of the system of FIG. 2 using a bellows arrangement in place of the main isolator;

DETAILED DESCRIPTION OF THE PREFERRED EMBODIMENTS

Figure 1:
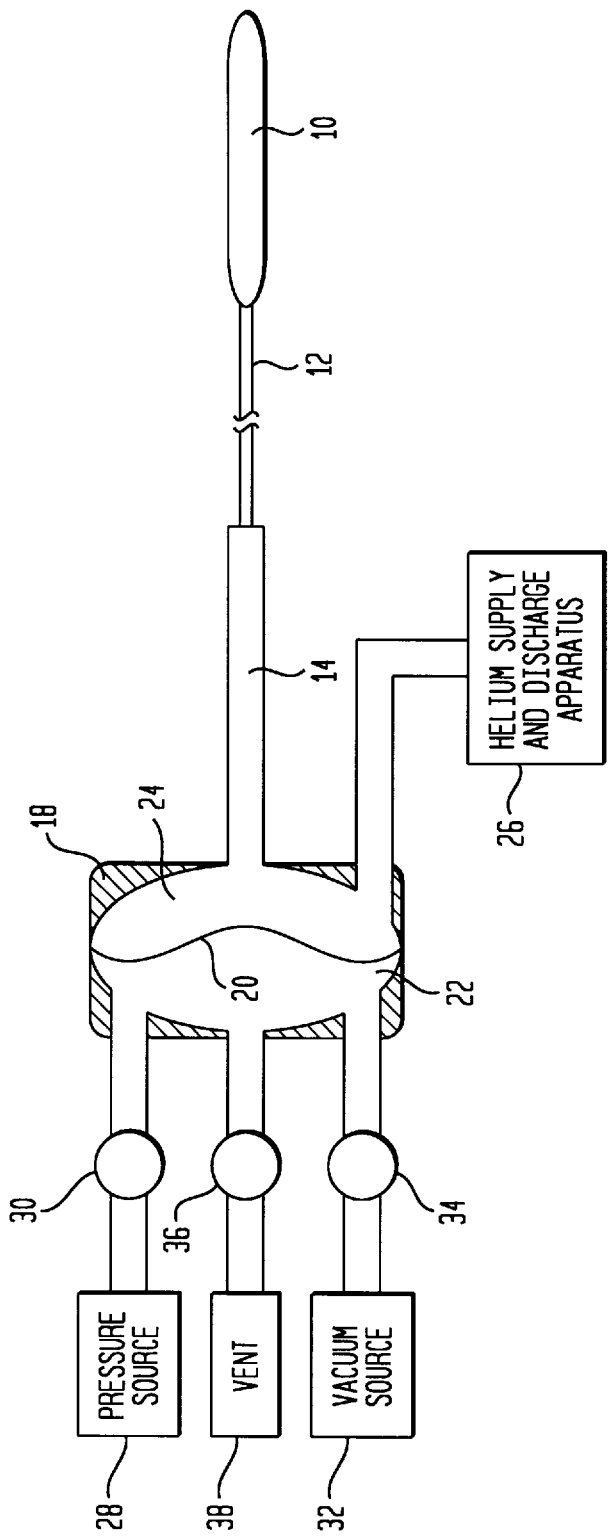
FIG. 1 is a highly schematic view showing a system for inflating and deflating an intra-aortic balloon in accordance with the prior art.
Figure 2:
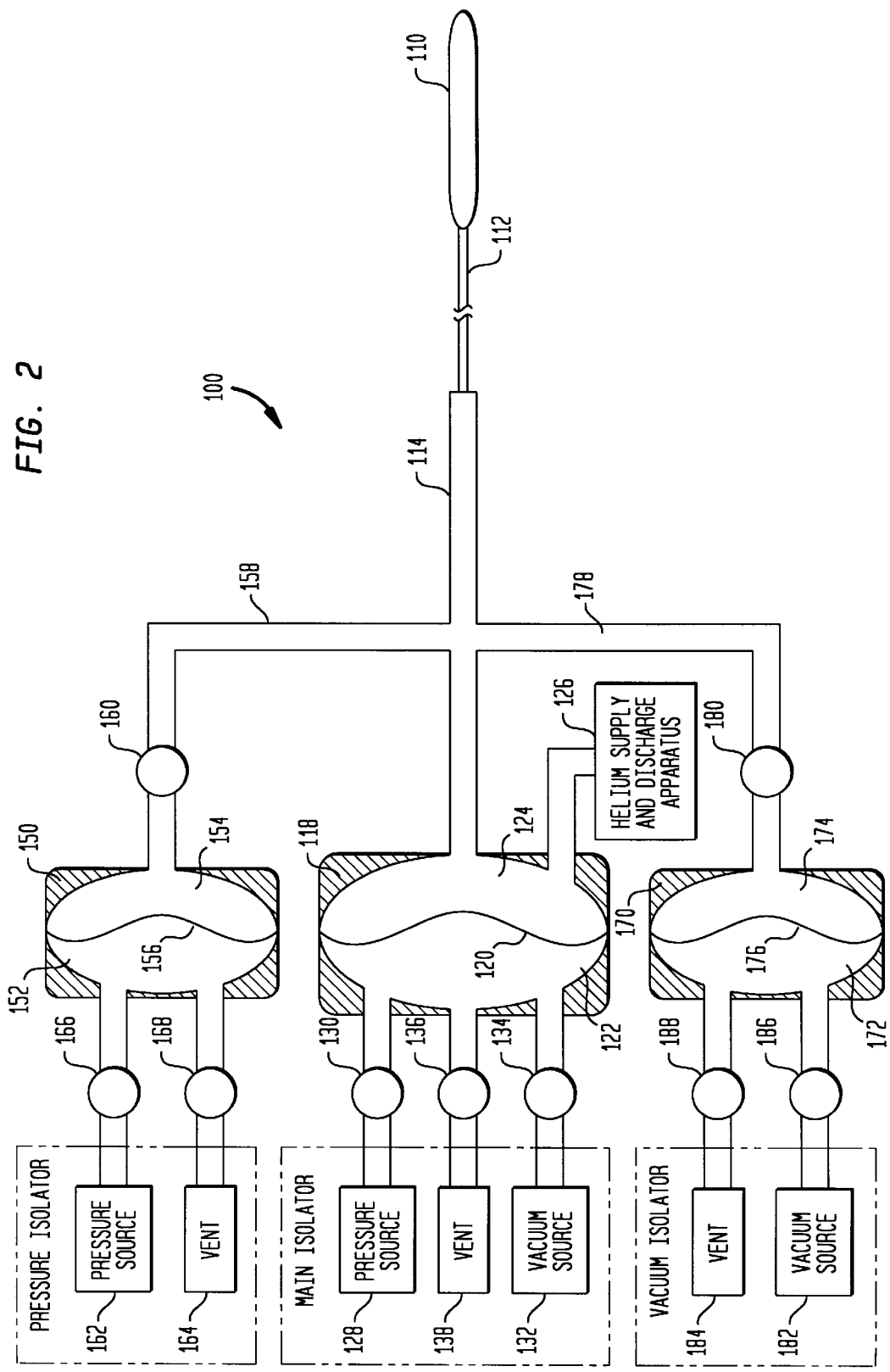
FIG. 2 is a highly schematic view showing a system for inflating and deflating an intra-aortic balloon in accordance with a first embodiment of the present invention.

One embodiment of an intra-aortic balloon pump 100 in accordance with the present invention is shown schematically in FIG. 2. A major portion of balloon pump 100 is similar to the conventional balloon pump 10 described above. Thus, balloon pump 100 includes a main isolator 118 divided into a primary side 122 and a secondary side 124 by a pliant membrane 120. Connected to the primary side 122 of the isolator 118 are a positive pressure source 128, such as an air compressor or other air supply, a negative pressure source 132, such as a vacuum pump or other vacuum source, and a vent port 138. A solenoid valve 130 controls the flow of air from the positive pressure source toward the isolator, a solenoid valve 134 controls the flow of air from the isolator toward the vacuum source, and a solenoid valve 136 controls the flow of air between the isolator and vent port 138. A controller (not shown) controls the operation of solenoid valves 130, 134 and 136 between the open and closed conditions.

On the opposite side of main isolator 118, an extender 114 and catheter 112 are connected in series with one another and with an intra-aortic balloon 110 so as to provide flow communication between balloon 110 and the secondary side 124 of isolator 118. A gas source, such as helium supply and discharge apparatus 126, is connected to the secondary side 124 of main isolator 118 to establish and maintain a predetermined volume of helium in the space between membrane 120 and balloon 110. As with the prior art system, extender 114 has a substantially larger diameter than catheter 112, such that the gas flows substantially unrestricted through extender 114, but is constricted in its flow through catheter 112.

In addition to the foregoing elements, balloon pump 100 of the present invention may include an auxiliary pressure isolator 150, an auxiliary vacuum isolator 170, or both. Pressure isolator 150 is similar in construction to main isolator 118, but has a smaller internal volume. Thus, pressure isolator 150 has a primary side 152 and a secondary side 154 divided by a pliant membrane 156. The secondary side 154 is connected in flow communication with extender 114 by a conduit 158 having substantially the same diameter as extender 114. A solenoid valve 160 controls the flow of gas between the secondary side 154 and extender 114. Connected to the primary side 152 of pressure isolator 150 are a source 162 of positive pressure, such as a compressor or other air supply, and a vent port 164. A solenoid valve 166 controls the flow of air from positive pressure source 162 to the primary side 152, and a solenoid valve 168 controls the flow of air between the primary side 152 and vent port 164. Solenoid valves 160, 166 and 168 are moved between the opened and closed conditions by the controller, mentioned above.

Vacuum isolator 170 is similar in construction to the other isolators, and includes a primary side 172 separated from a secondary side 174 by a pliant membrane 176. Secondary side 174 is connected in flow communication with extender 114 by a conduit 178 having a diameter which is substantially the same as the diameter of extender 114. A solenoid valve 180 controls the flow of gas in conduit 178 between extender 114 and the secondary side 174. Connected to the primary side 172 of vacuum isolator 170 are a negative pressure source 182, such as a vacuum pump or other vacuum source, and a vent port 184. A solenoid valve 186 controls the flow of air from primary side 172 toward vacuum source 182, and a solenoid valve 188 controls the flow of air between primary side 172 and vent port 184. As with the other valves in the system, the controller controls movement of solenoid valves 180, 186 and 188 between the open and closed conditions.

The operation of balloon pump 100 to inflate and deflate intra-aortic balloon 110 will now be described with reference to the graphs of FIG. 3. In the graphs, the solid line represents the operation of the system of the present invention, and the dashed line represents the operation of the system of the prior art. Assuming that the sequence starts with balloon 110 in a fully deflated condition, at time t=0, extender 114 and balloon 110 are at an end deflation pressure of about −2 psi, the balloon has an internal volume of about 0 cc, and all of solenoid valves 130, 134, 136, 160, 166, 168, 180, 186 and 188 are in a closed state. This starting point is represented by time A in the graphs. The controller then actuates valves 130, 160 and 166 to open, whereupon air pressure at about 8 psi from positive pressure source 128 pressurizes the primary side 122 of main isolator 118, forcing membrane 120 toward the secondary side 124 thereof, and air pressure at about 8 psi from positive pressure source 162 pressurizes the primary side 152 of pressure isolator 150, driving membrane 156 thereof toward the secondary side 154. The movement of membrane 120 forces the helium within the secondary side 124 toward and into extender 114, while the movement of membrane 156 forces the helium within the secondary side 154 through valve 160 toward and into extender 114, the helium from both isolators together producing a pressure in the extender which is about the same as the 8 psi pressure provided by positive pressure sources 128 and 162. As a result of the pressure differential created across catheter 112, some of this helium flows through the catheter to balloon 110 and the balloon begins to inflate, producing an immediate pressure within the balloon approximately equal to the blood pressure of the patient, e.g. about 2 psi. This point in the inflation cycle is represented by time B in the graphs. Because of its small diameter, helium flow through catheter 112 is constricted such that a pressure differential of about 6 psi (8 psi in the extender minus 2 psi in the balloon) continues to be maintained across the catheter, causing helium to continue to flow from extender 114 through catheter 112 to balloon 110.

Since more helium molecules are displaced by isolators 118 and 150 together than by isolator 118 alone, the maximum pressure of about 8 psi will be maintained in extender 114 longer than with the prior art system. That is, the buildup of pressure in extender 114 to 8 psi prevents one or both of membranes 120 and 156 from immediately reaching their fully extended positions against the wall on the secondary sides of their respective isolators. Therefore, as helium flows through catheter 112 to inflate balloon 110, the membranes which have not yet reached their fully extended positions continue to move forward to replace the helium leaving extender 114 with helium from the secondary sides of their isolators, thus maintaining the pressure in the extender at a substantially constant level throughout the dynamic portion of the inflation cycle, i.e., the portion of the cycle in which the balloon is inflating. As a result, the pressure differential across catheter 112 is maintained at about 6 psi for a longer interval than with the prior art system in which there is no "makeup" or excess helium to replace the helium flowing toward balloon 110. Since the maximum pressure differential is maintained across catheter 112 for a longer period of time, balloon 110 is inflated more quickly with the system of the present invention than with the system of the prior art.

Figures 3A, 3B, 3C:
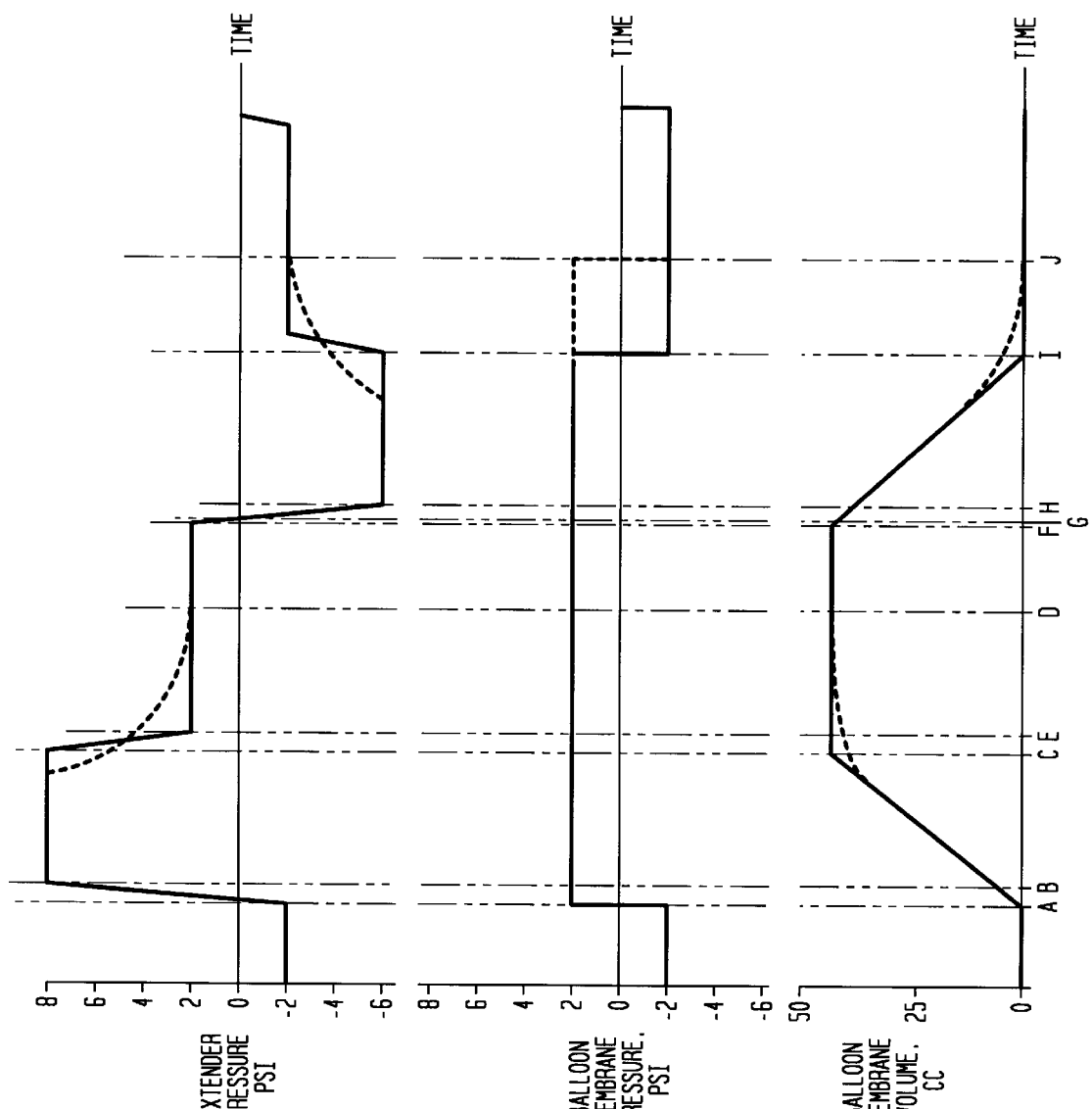
FIG. 3 is a series of graphs showing the relationship between the pressure in the extender and the pressure and volume in the intra-aortic balloon during the inflation and deflation cycles using the system shown in FIG. 2.

The more rapid inflation of balloon 110 with the system of the present invention is shown graphically in FIG. 3. Between times A and B, the system of the prior art and the system of the present invention produce substantially the same effect. At some time after time B, however, the effects differ. In the prior art system, the pressure in extender 114 begins to decrease as the balloon continues to inflate. This decreasing pressure results in a steadily decreasing pressure differential and, hence, a steadily decreasing flow rate across catheter 112, such that balloon 110 does not reach the desired inflation volume of about 40 cc until time D. With the present invention, however, the pressure in extender 114 is maintained substantially constant from time B until inflation has been completed at time C, such that the flow rate across catheter 112 does not decrease and the balloon reaches the desired inflation volume sooner.

By designing isolators 118 and 150 to have an appropriate total volume, as described in more detail below, balloon 110 will be substantially fully inflated when membranes 120 and 156 both have reached their fully extended position. At this point, the controller operates to close valves 130 and 166, and to open valve 168. The closure of valves 130 and 166 terminates the application of positive pressure to isolators 118 and 150, respectively. Therefore, as valve 168 is opened, the air pressure within the primary side 152 of isolator 150 is vented through port 164 to the atmosphere, such that the pressure on primary side 152 becomes less than the pressure on secondary side 154. Membrane 156 is forced by this pressure differential to its fully retracted position against the wall on primary side 152. As a result, a volume of the helium within extender 114 equal to the volume of isolator 150 flows through valve 160 to the secondary side 154 of isolator 150 until equilibrium is reached, lowering the pressure in extender 114 to about the same pressure as in balloon 110, i.e., about 2 psi, as shown at time E in FIG. 3. By lowering the pressure in extender 114 to about the same pressure as in balloon 110, this venting step prevents the balloon from becoming overinflated. It also reduces the amount of helium that must be removed from extender 114 during the deflation cycle, discussed below, thereby shortening the duration of that cycle. Since the pressure on the primary side 122 of isolator 118 has not been vented, membrane 120 at this point is still in its fully extended position against the isolator wall on secondary side 124. Valves 160 and 168 are subsequently closed.

Once the inflation cycle described above has been completed, the controller actuates appropriate valves to deflate balloon 110. As a first step, valve 136 is opened momentarily at time F to release the positive pressure from the primary side 122 of isolator 118 to the atmosphere through vent port 138, causing membrane 120 to begin moving toward primary side 122 and the pressure in extender 114 to decrease toward atmospheric pressure. Since the helium in extender 114 at the beginning of the deflation cycle was at about the same pressure as the helium in balloon 110, as the pressure in the extender decreases, the balloon begins to deflate. At time G shortly thereafter, when the pressure in extender 114 has reached about zero, i.e. atmospheric pressure, valve 136 is closed and valves 134, 180 and 186 are opened so that negative pressure at about −6 psi from vacuum source 132 evacuates the primary side 122 of isolator 118, drawing membrane 120 toward the wall on primary side 122, and negative pressure at about −6 psi from vacuum source 182 evacuates the primary side 172 of vacuum isolator 170, drawing membrane 176 thereof toward the wall on primary side 172. This movement of membranes 120 and 176 toward the primary sides of their respective isolators draws a volume of helium equal to the volume of isolator 118 out from extender 114 and into secondary side 124, and another volume of helium equal to the volume of isolator 170 out from extender 114 through valve 180 and into secondary side 174. This movement of helium out from the extender and into the isolators reduces the pressure in the extender significantly, and, more particularly, to about the same pressure of about −6 psi as provided by vacuum sources 132 and 182, as shown at time H. The constricted flow of helium through the small diameter of catheter 112 causes a pressure differential of about 8 psi (2 psi in the balloon minus −6 psi in the extender) to be maintained across the catheter, so that helium continues to flow out from balloon 110 through catheter 112 to extender 114.

As was the case with isolators 118 and 150 during the inflation cycle, isolators 118 and 170 together produce a greater volume displacement of helium than is produced by isolator 118 alone. Therefore, when the pressure in extender 114 has reached −6 psi, equal pressures on the primary and secondary sides of the isolators may prevent one or both of membranes 120 and 176 from immediately reaching their fully retracted positions against the wall on the primary sides of their respective isolators. As helium continues to flow out from balloon 110 through catheter 112, increasing the pressure in extender 114 and thus in the secondary sides of the isolators, the membranes which have not yet reached their fully retracted positions continue to move toward the primary sides of their isolators to increase the volume of the secondary sides, thus maintaining the pressure therein and in the extender at a substantially constant level throughout the dynamic portion of the deflation cycle, i.e., the portion of the cycle in which the balloon is deflating. As a result, the pressure differential across catheter 112 is maintained at about 8 psi for a longer interval than with the prior art system. Since the maximum pressure differential is maintained across catheter 112 for a longer period of time, balloon 110 is deflated more quickly with the system of the present invention than with the prior art system.

Here again, FIG. 3 provides a graphical illustration of the more rapid deflation of balloon 110 using the system of the present invention. Between times F and H at the beginning of the deflation cycle, the system of the prior art and the system of the present invention produce substantially the same effect. The effects produced, however, differ at some time after time H. In the prior art system, the pressure in extender 114 begins to gradually increase as the balloon begins to deflate. This gradually increasing pressure in the extender results in a steadily decreasing pressure differential, and therefore a steadily decreasing flow rate, across catheter 112. As a result of this decreasing flow, balloon 110 does not reach a substantially fully deflated condition until time J. On the other hand, the system of the present invention maintains the pressure in extender 114 at a substantially constant level from time H until substantially complete deflation has been reached at time I, such that the pressure differential and, hence, the flow rate across catheter 112 does not decrease, and the balloon reaches a substantially fully deflated condition more quickly.

Desirably, balloon 110 will be substantially fully deflated when membranes 120 and 176 both have reached their fully retracted positions against the wall on primary sides 122 and 172, respectively. When this occurs, the controller operates to close valves 134 and 186, terminating the application of negative pressure to isolators 118 and 170, respectively, and then to open valve 188. With valve 188 open, outside air is drawn through vent port 184 into primary side 172 of isolator 170, and membrane 176 toggles from primary side 172 to its fully extended position against the wall on secondary side 174. As a result, the helium within secondary side 174 is forced through valve 180 into extender 114, as well as into the secondary side 124 of isolator 118. The net result is that the pressure in extender 114 and in the secondary side 124 of isolator 118 is raised to an end deflation pressure above the level of the negative pressure supplied by vacuum sources 132 and 182, but still low enough that balloon 110 remains fully deflated. Desirably, isolator 170 is sized to produce an end deflation pressure of about −2 psi. Valves 180 and 188 are then closed.

As noted above, the effective operation of the system of the present invention is dependent upon the proper sizing of pressure isolator 150 and vacuum isolator 170, as well as main isolator 118. The helium-containing portion of system 100 is a substantially closed system, i.e., the total number of molecules of helium within the system remains essentially constant. This principle of mass conservation may be used to calculate the volumes of isolators 150 and 170. Since the number of molecules of helium in any one portion of the system at a given time is proportional to the pressure in that portion of the system at that time multiplied by its volume (assuming constant temperature), the volume of pressure isolator 150 can be approximated by comparing two different points in time during an inflation cycle, one point at which pressure isolator 150 is filled with helium, and another point at which it has no helium.

At the point when balloon 110 has been fully inflated, i.e. membrane 156 has reached the wall of isolator 150 on secondary side 154 and membrane 120 has reached the wall of isolator 118 on secondary side 124, all of the helium molecules in the system will be in extender 114, conduits 158 and 178, catheter 112 and balloon 110. Because catheter 112 has a very small volume in comparison to the other components, the number of molecules of helium in the catheter is negligible and can be assumed to be zero. Therefore, at this point in the inflation cycle, the total amount of helium in the system is given by the equation $$C_1 = P_E V_E + P_B V_B \tag{1}$$

where $C_1$ is some constant, $P_E$ is the absolute pressure in the extender, $V_E$ is the volume of the extender, including the volume of conduits 158 and 178 joined to the extender, $P_B$ is the absolute pressure in the balloon, and $V_B$ is the volume of the balloon.

At the point in time during the inflation cycle when valve 168 is opened to vent isolator 150, membrane 156 will be forced immediately against the wall of isolator 150 on primary side 152, and helium will flow from extender 114 into the secondary side 154. Hence, the total amount of helium ($C_2$) in the system at this point in time is given by the equation $$C_2 = P_I V_I + P_E V_E + P_B V_B \tag{2}$$

where $P_I$ is the absolute pressure in isolator 150 and $V_I$ is the volume in isolator 150. By making isolator 150 an appropriate volume, a sufficient amount of helium will flow from extender 114 to isolator 150 to create an equilibrium pressure in isolator 150 and extender 114 which is substantially equal to the pressure in balloon 110. Accordingly, formula (2) above can be rewritten $$C_2 = P_B(V_I + V_E + V_B). \tag{3}$$

Since the total amount of helium in the system is constant, $C_1$ equals $C_2$ and $$P_E V_E + P_B V_B = P_B(V_I + V_E + V_B).$$

Solving for the volume of isolator 150, $$V_I = \frac{P_E V_E + P_B V_B}{P_B} - V_E - V_B. \tag{4}$$

The volume of vacuum isolator 170 can be determined in a similar fashion by comparing two different points in time during a deflation cycle, one point at which vacuum isolator 170 is filled with helium, and another point at which it has no helium. At the point in the deflation cycle when membrane 176 has reached the wall of isolator 170 on primary side 172 and membrane 120 has reached the wall of isolator 118 on primary side 122, it is assumed that balloon 110 is fully deflated and has no volume, and therefore all of the helium in the system will be in extender 114, conduits 158 and 178, secondary side 124 of isolator 118 and secondary side 174 of isolator 170. Again, because of its small volume, the amount of helium in catheter 112 is assumed to be zero. Thus, at this instant, the total amount of helium ($C_3$) in the system is given by the equation $$C_3 = P_{MI} V_{MI} + P_{VI} V_{VI} + P_E V_E \tag{5}$$

where $P_{MI}$ is the absolute pressure in main isolator 118, $V_{MI}$ is the volume of main isolator 118, $P_{VI}$ is the absolute pressure in vacuum isolator 170, $V_{VI}$ is the volume of vacuum isolator 170, $P_E$ is the absolute pressure in extender 114, and $V_E$ is the volume of extender 114, including the volume of conduits 158 and 178 joined to the extender. Because main isolator 118, vacuum isolator 170 and extender 114 are in flow communication with one another, the pressure in each of these components will be about the same and, with an isolator 170 of an appropriate volume, will be substantially equal to the vacuum pressure (in absolute units), $P_{VAC}$, exerted on the system. Accordingly, equation (5) above can be rewritten $$C_3 = P_{VAC}(V_{MI} + V_{VI} + V_E). \quad (6)$$

At the point in time during the deflation cycle when valve 188 is opened to vent isolator 170, membrane 176 will be forced immediately against the wall of isolator 170 on secondary side 174, and helium will flow from isolator 170 into extender 114 and the secondary side of isolator 118. Thus, the total amount of helium ($C_4$) in the system at this point in time is given by the equation $$C_4 = P_{MI} V_{MI} + P_E V_E. \quad (7)$$

Here again, the main isolator and the extender will be at the same pressure which, in an appropriately designed system, will be an end deflation pressure (in absolute units), $P_D$, which is greater than the vacuum pressure of the system, but sufficiently low that balloon 110 remains fully deflated. Thus, equation (7) can be rewritten $$C_4 = P_D(V_{MI} + V_E). \quad (8)$$

Since the total amount of helium in the system is constant, $C_3$ equals $C_4$ and $$P_{VAC}(V_{MI} + V_{VI} + V_E) = P_D(V_{MI} + V_E).$$

Solving for the volume of isolator 170, $$V_{VI} = \frac{P_D(V_{MI} + V_E)}{P_{VAC}} - V_{MI} - V_E. \quad (9)$$

In a typical intra-aortic balloon pump, main isolator 118 may have a volume of about 73.4 cc, extender 14 may have a volume of about 38.6 cc and balloon 110 may have a volume of about 40.0 cc. Under normal operating conditions, when balloon 110 has been fully inflated, the pressure in the balloon win be the blood pressure of the patient, i.e. about 2 psi, and the pressure in extender 114 will be about the same as the pressure applied by pressure sources 128 and 162, i.e. about 8 psi. Plugging these numbers into equation (4), $$V_I = \frac{(14.6 + 8)(38.6) + (14.6 + 2)(40)}{(14.6 + 2)} - 38.6 - 40$$

where 14.6 is atmospheric pressure in psi for the purpose of converting gauge pressures to absolute pressures. Solving the above equation yields a volume for isolator 150 of about 14 cc.

When balloon 110 has been fully deflated, the end deflation pressure in the main isolator and extender, $P_D$, desirably is about −2 psi. Using a vacuum pressure, $P_{VAC}$, exerted on the system by negative pressure sources 132 and 182 of −6 psi and solving equation (9) to determine the volume of isolator 170, $$V_{VI} = \frac{(14.6 - 2)(73.4 + 38.6)}{14.6 - 6} - 73.4 - 38.6$$

Solving the above equation yields a volume for isolator 170 of about 52.1 cc.

The features of the present invention may be used in connection with intra-aortic balloon pumps which utilize an arrangement other than a main isolator for the controlled inflation and deflation of the balloon. One such system, sold by Arrow International Investment Corp. of Everett, Mass. under the trademark KAAT II PLUS, utilizes a bellows to effect inflation and deflation. An embodiment of an intra-aortic balloon pump 200 in accordance with this variant is shown schematically in FIG. 4. Balloon pump 200 is similar to balloon pump 100 described above. However, in place of main isolator 118, balloon pump 200 includes a bellows 210 having a rigid stationary front plate 212, a rigid movable back plate 214 and an expandable and collapsible side wall 216. The shaft 220 of a stepper motor 222 is threadedly connected to back plate 214 through a lead screw 224 so that rotation of stepper motor 222 in a forward or reverse direction results in a corresponding forward or backward linear movement of bellows back plate 214.

To inflate intra-aortic balloon 110 from a fully deflated condition using balloon pump 200, a controller (not shown) initially actuates stepper motor 222 to rotate shaft 220 a predetermined number of revolutions in, for example, a clockwise direction so as to push bellows back plate 214 forward. This motion has the effect of reducing the internal volume of bellows 210 by a predetermined amount, forcing a portion of the helium in the bellows into extender 114 and creating a pressure differential across catheter 112 to inflate the balloon. At the same time that stepper motor 222 is actuated, valves 160 and 166 are opened, whereupon the helium within the secondary side 154 of pressure isolator 150 is pushed toward and into extender 114. Because more helium molecules are displaced by bellows 210 and isolator 150 together than by bellows 210 alone, membrane 156 does not immediately reach its fully extended position, but rather continues to move forward to replace the helium leaving the extender and flowing through catheter 112 to inflate balloon 110. Accordingly, the pressure differential across catheter 112 is maintained at a maximum level throughout the inflation cycle, such that balloon 110 is inflated more quickly than with the prior art system.

By using an isolator 150 having an appropriate volume, as described above, balloon 110 will be substantially fully inflated when membrane 156 has moved to its fully extended position against the wall on the secondary side 154 of the isolator. When this occurs, the controller operates to close valve 166, terminating the application of positive pressure to isolator 150, and to open valve 168 in order to vent the air pressure within the primary side 152 of the isolator out through vent port 164. This step has the effect of moving membrane 156 to its fully retracted position against the wall on primary side 152 and reducing the pressure in extender 114 and bellows 210 to about the same pressure as in balloon 110. Valves 160 and 168 are subsequently closed.

The deflation cycle for balloon pump 200 may operate in a similar manner. Unlike balloon pump 100 described above, there is no air in bellows 210, and therefore no need to initiate the deflation cycle with a venting step. Rather, to begin the deflation cycle, stepper motor 222 is actuated to rotate shaft 220 a predetermined number of revolutions in a counterclockwise direction so as to pull bellows back plate 214 rearward. This motion has the effect of increasing the internal volume of bellows 210 by a predetermined amount so as to create a negative pressure therein, drawing a portion of the helium from extender 114 into the bellows. As a result, the pressure in the extender is reduced to a level below the pressure in the balloon and a flow of helium is created from balloon 110 to extender 114 to deflate the balloon. At the same time that stepper motor 222 is actuated, valves 180 and 186 are opened, whereupon vacuum source 182 creates a negative pressure on the primary side 172 of vacuum isolator 170, pulling membrane 176 thereof toward the wall on primary side 172 and drawing a volume of helium equal to the volume of isolator 170 out from extender 114. These additional helium molecules drawn out from the extender keep the extender at a low pressure for a longer period of time so that balloon 110 deflates more quickly. Once membrane 176 has reached its fully retracted position against the wall on primary side 172, valve 186 is closed, terminating the application of negative pressure to isolator 170, and valve 188 is opened in order to bring the pressure on primary side 172 back up to atmospheric pressure. This has the effect of toggling membrane 176 to the wall on secondary side 174, pushing the helium therein toward and into extender 114. By using an isolator 170 having an appropriate volume, as described above, this helium flow will increase the pressure in the extender and in the bellows to the desired end deflation pressure, preferably about –2 psi. Subsequently, valves 180 and 188 are closed.

The use of an auxiliary pressure isolator and/or an auxiliary vacuum isolator in combination with still other arrangements for the controlled inflation and deflation of balloon 110 is also contemplated by the present invention. Thus, for example, rather than main isolator 118 or bellows 210, the inflation and deflation of balloon 110 may be effected by a system incorporating a piston reciprocally movable in a sleeve so that movement of the piston in a forward direction pushes gas into the extender and movement of the piston in a backward direction draws gas out from the extender. Inflation and deflation may also be effected by a system incorporating a turbine rotatably mounted between a fixed volume chamber and the extender so that rotation of the turbine in one direction draws gas from the chamber and pushes it into the extender, and rotation of the turbine in the opposite direction draws gas away from the extender and pushes it into the chamber. A still further system may include a pressure source, a vacuum source and a vent port mounted through solenoid valves directly to the extender, such that operation of each solenoid valve for a predetermined length of time would produce the desired pressure in the extender. Any arrangement for effecting the inflation and deflation of balloon 110 other than those described above are also contemplated herein.

Figure 5:
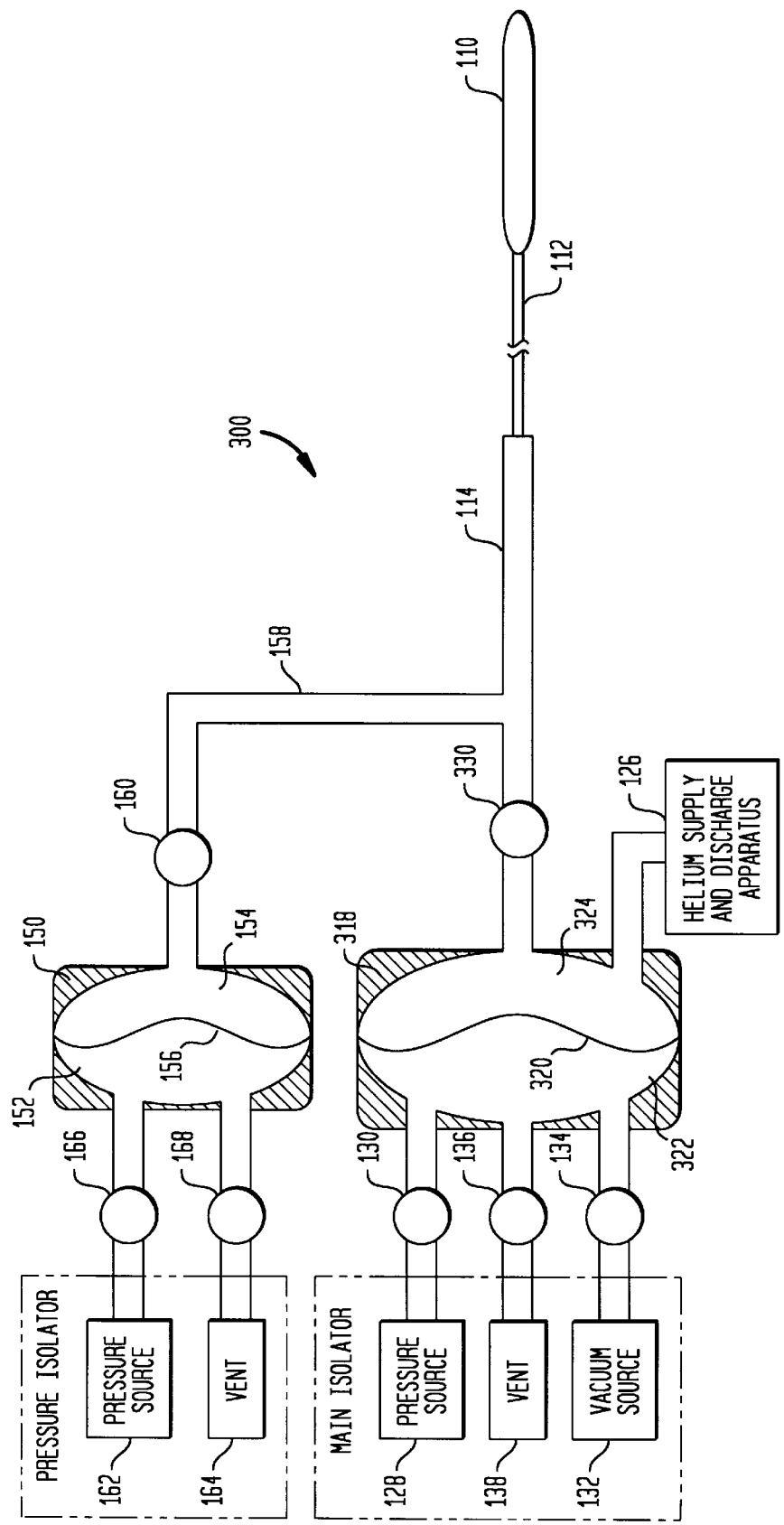
FIG. 5 is a highly schematic view showing a system for inflating and deflating an intra-aortic balloon in accordance with a second embodiment of the present invention.

Another embodiment of an intra-aortic balloon pump 300 in accordance with the present invention is shown in FIG. 5. Balloon pump 300 is similar in configuration to balloon pump 100 described above, but includes an oversized main isolator 318, i.e., an isolator having a volume which is significantly larger than the volume of conventional main isolator 118. A pliant membrane 320 divides main isolator 318 into a primary side 322 and a secondary side 324. As with main isolator 118 described above, connected to the primary side 322 of isolator 318 are a positive pressure source 128, a negative pressure source 132 and a vent port 138, with solenoid valves 130, 134 and 136 controlling the flow between these components and the isolator. Balloon pump 300 also differs from balloon pump 100 in that it does not include a vacuum isolator 170 or the solenoid valves or vacuum source associated therewith. In addition, as described below, balloon pump 300 optionally may include a solenoid valve 330 positioned between isolator 318 and extender 114.

The operation of balloon pump 300 to inflate balloon 110 is substantially the same as described above in connection with balloon pump 100. That is, starting with balloon 110 in a fully deflated condition, membranes 156 and 320 will be in their fully retracted positions and valves 130, 134, 136, 160, 166 and 168 will be closed. To start inflation, valves 130, 160 and 166 are opened to pressurize isolators 150 and 318 and force membranes 156 and 320 toward the secondary sides thereof, inflating the balloon. When membranes 156 and 320 both have moved fully forward against the wall on the secondary sides of their isolators, balloon 110 will be substantially fully inflated. The controller then operates to close valves 130 and 166, terminating the application of positive pressure to the primary sides of isolators 150 and 318, and to open valve 168 so as to vent the pressure from the primary side 152 of isolator 150 to the atmosphere. This causes membrane 156 to toggle to its fully retracted position against the wall on primary side 152, drawing helium out from extender 114 and from the secondary side of isolator 318 and into secondary side 154 of isolator 150, thus lowering the pressure in extender 114 and secondary side 324 to about the same 2 psi pressure as in balloon 110. Valves 160 and 168 are then closed.

The deflation sequence may then be initiated by momentarily opening valve 136 to vent the pressure from primary side 322 of isolator 318 to the atmosphere, causing balloon 110 to begin to deflate. After the pressure in primary side 322 has reached about atmospheric pressure, valve 136 is closed and valve 134 is opened to apply negative pressure to primary side 322, drawing membrane 320 toward the wall on the primary side. Because isolator 318 is oversized, it produces a result which is similar to the result produced by the combined action of main isolator 118 and vacuum isolator 170 described above. That is, the movement of membrane 320 toward primary side 322 draws a volume of helium out from extender 114 which is greater than the amount drawn out by conventionally sized main isolator 118. When membrane 320 reaches its fully retracted position, balloon 110 is fully deflated, and valve 134 is closed. Valve 136 may then be opened briefly to partially vent the negative pressure in primary side 322 of isolator 318. When membrane 320 has moved a sufficient amount toward secondary side 324 to produce a desired end deflation pressure in extender 114 and secondary side 324, valve 136 is closed. An end deflation pressure of about –2 psi is particularly desirable.

It will be appreciated from the foregoing description of the operation of balloon pump 300 that the volume of main isolator 318 should be approximately equal to the combined volumes of main isolator 118 and vacuum isolator 170 described above. For any particular arrangement, this volume can be calculated by comparing the pressure and volume values for the system at two appropriate points in time during a deflation cycle using the principle of mass conservation described above.

As noted previously, in a variant of this embodiment, balloon pump 300 may include a valve 330 positioned between isolator 318 and extender 114. In accordance with this variant, inflation and deflation proceed as described above, with valve 330 in an open condition. When balloon 110 has reached its fully deflated condition, membranes 156 and 320 both will be in their fully retracted positions against the wall on the primary sides of their respective isolators, valves 134 and 330 will be open, and valves 130, 136, 160, 166 and 168 will be closed. Valve 330 is then closed and valves 160 and 168 are opened. Since the atmospheric pressure on the primary side 152 of isolator 150 is larger than the deflation pressure on secondary side 154, membrane 156 is toggled to its fully extended position on secondary side 154, pushing the helium from the secondary side into extender 114, and creating therein the desired end deflation pressure. Valves 160 and 168 are then closed and valve 136 is opened briefly to bring the pressure in primary side 322 of isolator 318 to atmospheric pressure. The next inflation cycle would begin from this point, but would include the opening of valve 330 in addition to valves 130, 160 and 166. Although membranes 156 and 320 will not be in their fully retracted positions to start the cycle as described above in connection with the other variant of this embodiment, that does not change the sequence of events in the inflation cycle. Rather, it merely means that the membranes do not have to move or have a shorter distance to move on pressurization of the primary sides of the isolators.

Figure 6:
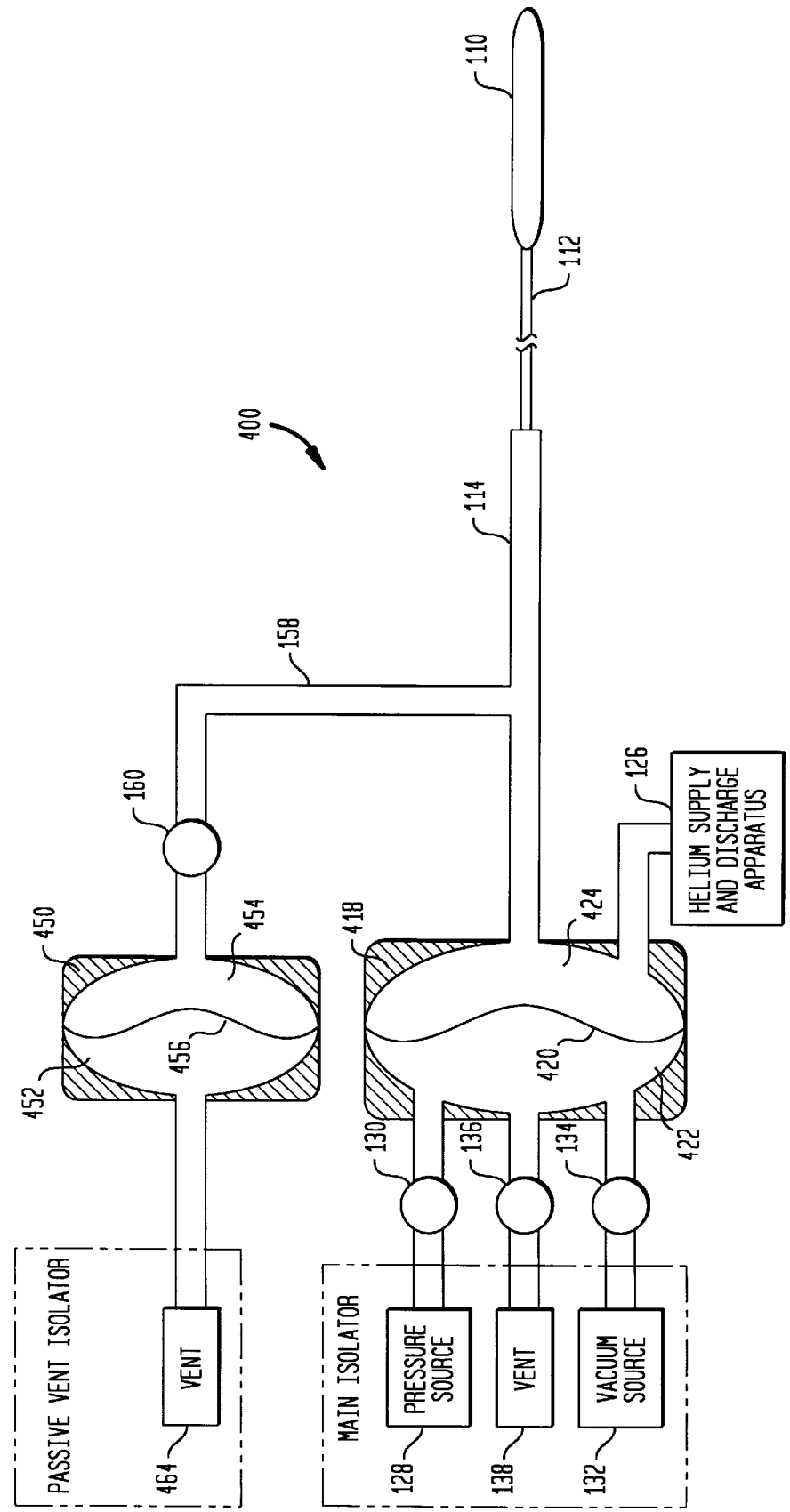
FIG. 6 is a highly schematic view showing a system for inflating and deflating an intra-aortic balloon in accordance with a third embodiment of the present invention.

A third embodiment of an intra-aortic balloon pump 400 in accordance with the present invention is shown in FIG. 6. Balloon pump 400 is similar to balloon pump 300 described above, but includes a passive vent isolator 450 in place of pressure isolator 150. As with the other isolators, vent isolator 450 includes a pliant membrane 456 dividing its interior volume into a primary side 452 and a secondary side 454. A vent port 464 is connected to primary side 452. However, as will be appreciated from the discussion which follows, unlike the previous embodiments, there is no need for a solenoid valve for controlling the flow between vent port 464 and the primary side 452 of the vent isolator.

The inflation of balloon 110 using balloon pump 400 begins with membrane 420 in oversized main isolator 418 in its fully retracted position against the wall on primary side 422, membrane 456 in vent isolator 450 in its fully extended position against the wall on secondary side 454, valves 130, 134, 136 and 160 closed and balloon 110 fully deflated. To start inflation, valve 130 is opened to pressurize isolator 418 and move membrane 420 to its filly extended position on secondary side 424, moving the helium therein into extender 114, whereupon the balloon inflates. When membrane 420 reaches its fully extended position, balloon 110 will be substantially fully inflated. Since isolator 418 is oversized, a greater number of molecules of helium flow into extender 114, and balloon 110 therefore reaches full inflation more rapidly than in systems using a conventionally sized main isolator. At this moment, valve 130 is closed and valve 160 is opened, pushing membrane 456 to its fully retracted position and venting the air within primary side 452 out through vent port 464. This causes a portion of the helium in extender 114 to flow into secondary side 454, decreasing the pressure in extender 114 to a pressure which is about the same as the inflation pressure in balloon 110. Once this venting step has been completed, valve 160 is closed.

For deflation, valve 136 is opened momentarily to vent the positive pressure on primary side 422 of isolator 418 out through vent port 138. Valve 136 is closed when the pressure in primary side 422 has reached about atmospheric pressure, and valve 134 is opened to apply negative pressure to primary side 422, drawing membrane 420 to its fully retracted position. Again, since isolator 418 is oversized, the movement of membrane 420 toward primary side 422 draws a greater volume of helium out from extender 114 than with a conventionally sized isolator, such that balloon 110 is fully deflated when membrane 420 reaches its fully retracted position, which occurs more rapidly than with conventional isolators. At this point, valve 134 is closed and valve 160 is opened, causing membrane 456 to move to its fully extended position and the helium within secondary side 454 to move into extender 114 and the secondary side 424 of isolator 418. By appropriately sizing isolators 418 and 450, this last step has the effect of increasing the pressure in extender 114 and secondary side 424 to a desired end deflation pressure of about −2 psi. Valve 160 is then closed.

Figure 7:
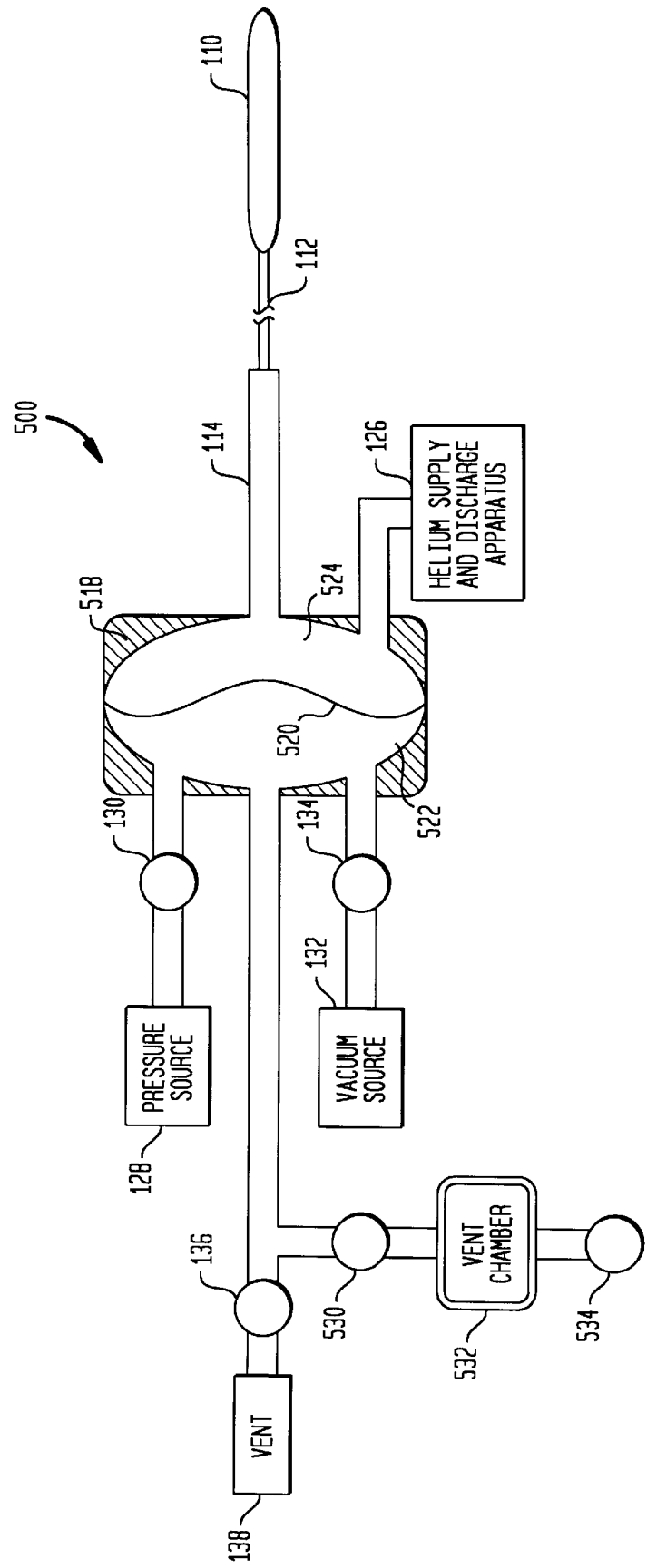
FIG. 7 is a highly schematic view showing a system for inflating and deflating an intra-aortic balloon in accordance with a fourth embodiment of the present invention.

A still further embodiment of an intra-aortic balloon pump 500 in accordance with the present invention is shown in FIG. 7. Balloon pump 500 utilizes an isolator 518 which also is larger in volume than conventional main isolator 118. As with the other isolators described above, isolator 518 is divided into a primary side 522 and a secondary side 524 by a pliant membrane 520. Connected to the primary side 522 of isolator 518 are a positive pressure source 128, a negative pressure source 132 and a vent port 138. A solenoid valve 130 controls the flow of air from the positive pressure source to the isolator, a solenoid valve 134 controls the flow of air from the isolator to the negative pressure source, and a solenoid valve 136 controls the flow of air between vent port 138 and the isolator. A vent chamber 532 having a fixed volume is connected in parallel with vent port 138, and includes a solenoid valve 530 for controlling the flow of air between the isolator and the vent chamber, and a solenoid valve 534 for controlling the flow of air between the vent chamber and the atmosphere.

The operation of balloon pump 500 to inflate balloon 110 will now be described starting from the fully deflated condition with membrane 520 in its fully retracted position on primary side 522, valves 130, 134, 136, 530 and 534 closed, and atmospheric pressure in vent chamber 532. To effect inflation, valve 130 is opened to pressurize primary side 522 of isolator 518, moving membrane 520 toward secondary side 524. This movement forces the helium from secondary side 524 into extender 114, raising the pressure therein so as to cause helium to flow across catheter 112 to inflate balloon 110. When membrane 520 has reached its fully extended position against the wall on secondary side 524, balloon 110 will be substantially fully inflated. Here again, because isolator 518 is larger than conventional isolators, a greater amount of helium is pushed into the extender such that full inflation is reached more rapidly. When full inflation is achieved, valve 130 is closed and valve 530 is opened, venting a predetermined volume of air out from primary side 522 into vent chamber 532. The size of vent chamber 532 will determine the volume of air vented from primary side 522 and, hence, the amount by which membrane 520 will retract toward primary side 522. Since the retraction of membrane 520 causes helium to flow from extender 114 into secondary side 524, by appropriately sizing vent chamber 532 the pressure in extender 114 may be lowered to about the same 2 psi pressure as in balloon 110. Valve 530 is then closed and valve 534 opened to vent the pressurized air from vent chamber 532 to the atmosphere, following which valve 534 is closed.

As the initial deflation step, valve 136 is opened to vent the remainder of the pressurized air from primary side 522 to the atmosphere through vent port 138. Because isolator 518 is oversized, this step does not cause membrane 520 to move to its fully retracted position on primary side 522. Rather, membrane 520 moves toward primary side 522 until equilibrium is reached with a pressure of about 0 psi on both sides of the membrane. With the pressure in extender 114 reduced to about 0 psi, balloon 110 begins to deflate. Valve 136 is then closed and valve 134 is opened to apply negative pressure to primary side 522, drawing membrane 520 to its fully retracted position on primary side 522. As with balloon pump 400 described above, the larger volume of isolator 518 causes a greater amount of helium to be drawn out of extender 114 than with conventionally sized isolators, such that balloon 110 deflates more quickly. When membrane 520 reaches its fully retracted position, balloon 110 is fully deflated, and valve 134 is closed. Valve 530 may then be opened to reduce the negative pressure (i.e., increase the pressure) in primary side 522 using the atmospheric pressure in vent chamber 532. As an alternative, the positive pressure from venting primary side 522 following inflation can be stored in vent chamber 532 and used during deflation venting to increase the pressure in primary side 522 to a greater extent. First venting vent chamber 532 to atmosphere, however, is preferable in that it produces a more consistent result from one cycle to the next.

Again, the volume of vent chamber 532 will determine the pressure increase in primary side 522 and, hence, the end deflation pressure in extender 114. Since the volume of vent chamber 532 determines both the end inflation pressure and the end deflation pressure in the extender, the vent chamber may be designed with a volume which is a compromise between the optimum volume for venting the positive pressure and the optimum volume for venting the negative pressure. Alternatively, balloon pump 500 may be provided with two vent chambers, one for use during the inflation cycle and one for use during the deflation cycle.

Figure 8:
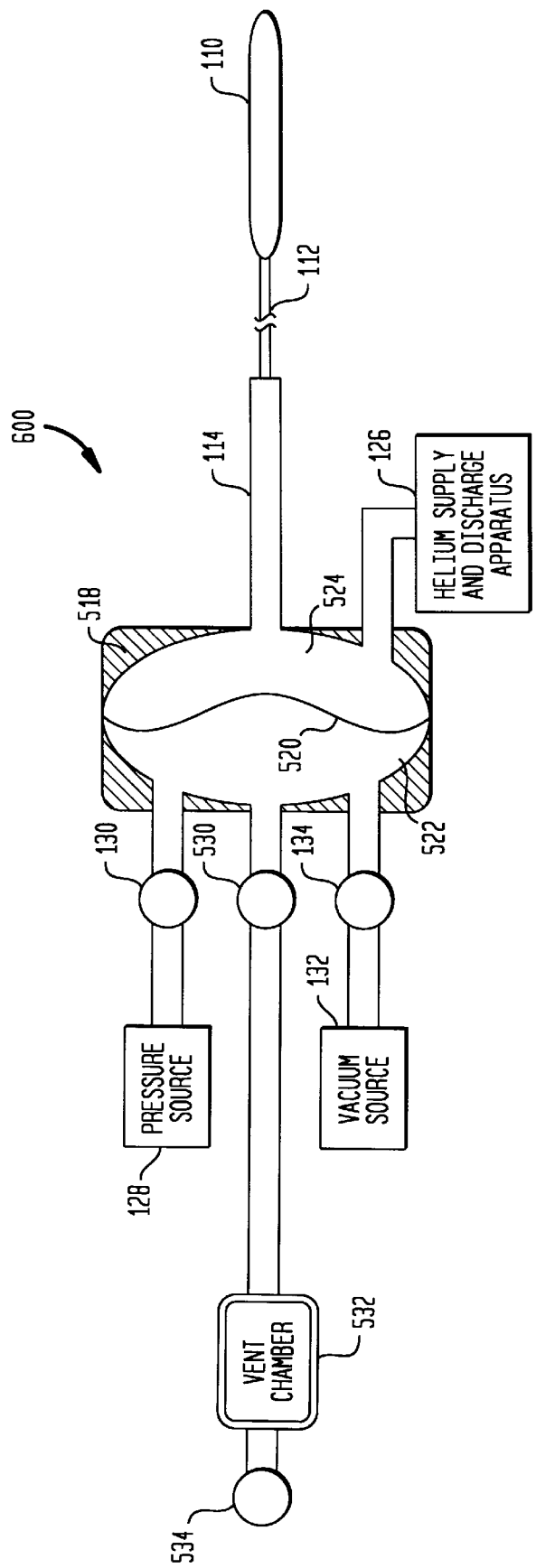
FIG. 8 is a highly schematic view showing a system for inflating and deflating an intra-aortic balloon in accordance with a fifth embodiment of the present invention.

Yet a further embodiment of an intra-aortic balloon pump 600 in accordance with the present invention is shown in FIG. 8. Balloon pump 600 is substantially the same as balloon pump 500 described above, but eliminates valve 136 and vent port 138. The operation of balloon pump 600 also is essentially the same as described above for balloon pump 500. However, after balloon 110 has been inflated and valve 530 has been opened to vent a predetermined volume of air from primary side 522 to vent chamber 532, valve 534 is opened to vent the remainder of the pressurized air from primary side 522 to the atmosphere through valve 530, vent chamber 532 and valve 534, whereupon balloon 110 begins to deflate. Valves 530 and 534 are subsequently closed and valve 134 is opened to fully deflate the balloon.

It will be appreciated that the principles of the present invention may be applied to intra-aortic balloon pumps which do not incorporate isolators in their configurations. For instance, the main isolator in any of balloon pumps 300, 400, 500 and 600 may be replaced with other arrangements for inflating and deflating balloon 110, such as the bellows, piston, turbine and direct drive arrangements described above. Regardless of the arrangement, during an inflation cycle helium would be supplied to the extender in an amount greater than the amount supplied by a conventional main isolator 118 so as to maintain a substantially constant pressure in the extender throughout the entire dynamic portion of the inflation cycle. When the balloon has been fully inflated, this excess helium would be removed from the extender by some venting step, resulting in an end inflation pressure in the extender which is about equal to the pressure in the balloon. For a deflation cycle, helium would be removed from the extender in an amount greater than the amount removed by a conventional main isolator 118 so as to maintain a substantially constant pressure in the extender throughout the dynamic portion of the deflation cycle. When the balloon has been fully deflated, an amount of helium substantially equal to the amount of this excess helium may be supplied to the extender, resulting in an end deflation pressure greater than the pressure in the extender during the dynamic portion of the deflation cycle, but not great enough to cause the balloon to begin to inflate.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as set forth in the appended claims.

We claim:

1. A method for inflating and deflating a medical device, said medical device being connected to a conduit having a first end connected to said medical device and a second end, said medical device and said conduit being filled with a working gas, said method comprising the steps of:

applying a first positive pressure to said working gas at said second end of said conduit;

maintaining said first positive pressure for a predetermined time to substantially fully inflate said medical device to a working pressure lower than said first positive pressure;

reducing the pressure at said second end of said conduit to a second positive pressure substantially equal to said working pressure; and reducing the pressure at said second end of said conduit to a third pressure lower than said second positive pressure to deflate said medical device.

2. The method as claimed in claim 1, wherein said first positive pressure is applied from first and second sources connected in parallel with one another.

3. The method as claimed in claim 2, wherein said step of applying said first positive pressure includes the steps of moving a first amount of said working gas from said first source toward said second end of said conduit and moving a second amount of said working gas from said second source toward said second end of said conduit.

4. The method as claimed in claim 3, wherein said second amount is less than said first amount.

5. The method as claimed in claim 3, wherein said second source includes a chamber having a predetermined volume, and said step of moving said second amount of said working gas includes the step of moving a volume of said working gas substantially equal to said predetermined volume from said chamber toward said second end of said conduit.

6. The method as claimed in claim 2, wherein said second source includes a chamber having a predetermined volume, and said step of reducing the pressure at said second end of said conduit to said second positive pressure includes the step of moving a volume of said working gas substantially equal to said predetermined volume from said second end of said conduit into said chamber.

7. The method as claimed in claim 1, wherein said step of applying said first positive pressure includes the step of moving a first amount of said working gas to said second end of said conduit, and said step of reducing the pressure at said second end of said conduit to said second positive pressure includes the step of removing a second amount of said working gas less than said first amount from said second end of said conduit.

8. The method as claimed in claim 7, wherein said step of reducing the pressure at said second end of said conduit to said third pressure includes the step of removing a third amount of said working gas from said second end of said conduit, said second amount and said third amount together being substantially equal to said first amount.

9. The method as claimed in claim 1, wherein said step of reducing the pressure at said second end of said conduit to said third pressure includes the steps of:

applying a first negative pressure to said working gas at said second end of said conduit;

maintaining said first negative pressure for a predetermined time to substantially fully deflate said medical device to a deflation pressure higher than said first negative pressure; and increasing the pressure at said second end of said conduit to a second negative pressure substantially equal to said deflation pressure.

10. The method as claimed in claim 9, wherein said first negative pressure is applied from first and second sources connected in parallel with one another.

11. The method as claimed in claim 10, wherein said second source includes a chamber having a predetermined volume, and said step of increasing the pressure at said second end of said conduit to said second negative pressure includes the step of moving a volume of said working gas substantially equal to said predetermined volume from said chamber toward said second end of said conduit.

12. The method as claimed in claim 10, wherein said step of applying said first negative pressure includes the steps of moving a first amount of said working gas from said second end of said conduit toward said first source and moving a second amount of said working gas from said second end of said conduit toward said second source.

13. The method as claimed in claim 12, wherein said second amount is less than said first amount.

14. The method as claimed in claim 12, wherein said second source includes a chamber having a predetermined volume, and said step of moving said second amount of said working gas includes the step of moving a volume of said working gas substantially equal to said predetermined volume from said second end of said conduit into said chamber.

15. The method as claimed in claim 9, wherein said step of applying said first negative pressure includes the step of removing a first amount of said working gas from said second end of said conduit, and said step of increasing the pressure at said second end of said conduit to said second negative pressure includes the step of supplying an amount of said working gas less than said first amount to said second end of said conduit.

16. A method for inflating and deflating a medical device, said medical device being connected to a conduit having a first end connected to said medical device and a second end connected to an operating apparatus, said medical device, said conduit and said operating apparatus being filled with a working gas, said method comprising the steps of:

placing said operating apparatus in an inflation condition to produce a pressure differential across said conduit with the pressure of said working gas in said operating apparatus at a first positive pressure and the pressure of said working gas in said medical device at a second positive pressure less than said first positive pressure, whereby said working gas flows from said operating apparatus to said medical device to inflate said medical device;

maintaining said pressure differential across said conduit for a predetermined time to substantially fully inflate said medical device to a working pressure lower than said first positive pressure;

placing said operating apparatus in an intermediate condition to reduce the pressure of said working gas in said operating apparatus to a second positive pressure substantially equal to said working pressure; and placing said operating apparatus in a deflation condition to reduce the pressure of said working gas in said operating apparatus to a third pressure lower than said second positive pressure, whereby gas flows from said medical device to said operating apparatus to deflate said medical device.

17. The method as claimed in claim 16, wherein said step of placing said operating apparatus in said inflation condition includes the steps of moving a first amount of said working gas from a first portion of said operating apparatus toward said second end of said conduit and moving a second amount of said working gas from an auxiliary portion of said operating apparatus toward said second end of said conduit.

18. The method as claimed in claim 17, wherein said second amount is less than said first amount.

19. The method as claimed in claim 17, wherein said step of placing said operating apparatus in said intermediate condition includes the step of reducing the pressure in said auxiliary portion to about said second positive pressure.

20. The method as claimed in claim 16, wherein said step of placing said operating apparatus in said deflation condition includes the steps of:

placing said operating apparatus in a first deflation condition to produce a pressure differential across said conduit with the pressure of said working gas in said operating apparatus at a first negative pressure and the pressure of said working gas in said medical device at said working pressure, whereby said working gas flows from said medical device to said operating apparatus to deflate said medical device;

maintaining said pressure differential across said conduit for a predetermined time to substantially fully deflate said medical device to a deflation pressure higher than said first negative pressure; and placing said operating apparatus in a second intermediate condition to increase the pressure in said operating apparatus to a second negative pressure substantially equal to said deflation pressure.

21. A medical apparatus, comprising an inflatable member;

a conduit having a first end connected to said inflatable member and a second end;

a working gas contained within said inflatable member and said conduit;

means for applying a first positive pressure to said working gas at said second end of said conduit;

a control device for maintaining said first positive pressure for a predetermined time to substantially fully inflate said inflatable member to a working pressure lower than said first positive pressure;

means for reducing the pressure at said second end of said conduit to a second positive pressure substantially equal to said working pressure; and means for reducing the pressure at said second end of said conduit to a third pressure lower than said second positive pressure to deflate said inflatable member.

22. The apparatus as claimed in claim 21, wherein said means for applying said first positive pressure includes a main positive pressure source and an auxiliary positive pressure source connected in parallel with one another.

23. The apparatus as claimed in claim 22, wherein said means for reducing the pressure at said second end of said conduit to said third pressure includes an auxiliary negative pressure source connected in parallel with said main positive pressure source.

24. The apparatus as claimed in claim 22, wherein said main positive pressure source includes a main chamber and said auxiliary positive pressure source includes an auxiliary positive pressure chamber having a fixed volume.

25. The apparatus as claimed in claim 24, wherein said main chamber has a volume greater than said fixed volume.

26. The apparatus as claimed in claim 24, wherein said means for reducing the pressure at said second end of said conduit to said second positive pressure includes said auxiliary positive pressure chamber.

27. The apparatus as claimed in claim 24, wherein said means for reducing the pressure at said second end of said conduit to said third pressure includes a main negative pressure source including said main chamber.

28. The apparatus as claimed in claim 21, wherein said means for reducing the pressure at said second end of said conduit to said third pressure includes a main negative pressure source and an auxiliary negative pressure source connected in parallel with one another.

29. The apparatus as claimed in claim 28, wherein said main negative pressure source includes a main chamber and said auxiliary negative pressure source includes an auxiliary negative pressure chamber having a fixed volume.

30. The apparatus as claimed in claim 29, wherein said main chamber has a volume greater than said fixed volume.

31. The apparatus as claimed in claim 21, wherein said means for reducing the pressure at said second end of said conduit to said third pressure includes means for applying a first negative pressure to said working gas at said second end of said conduit;

a control mechanism for maintaining said first negative pressure for a predetermined time to substantially fully deflate said medical device to a deflation pressure higher than said first negative pressure; and means for increasing the pressure at said second end of said conduit to a second negative pressure substantially equal to said deflation pressure.

32. The apparatus as claimed in claim 31, wherein said means for applying said first negative pressure includes a main negative pressure source and an auxiliary negative pressure source connected in parallel with one another.

33. The apparatus as claimed in claim 32, wherein said main negative pressure source includes a main chamber and said auxiliary negative pressure source includes an auxiliary negative pressure chamber having a fixed volume.

34. The apparatus as claimed in claim 33, wherein said main chamber has a volume greater than said fixed volume.

35. The apparatus as claimed in claim 33, wherein said means for increasing the pressure at said second end of said conduit to said second negative pressure includes said auxiliary negative pressure chamber.

36. The apparatus as claimed in claim 21, wherein said means for applying said first positive pressure includes a positive pressure source including a main chamber, and said means for reducing the pressure at said second end of said conduit to said second positive pressure includes an auxiliary chamber having a fixed volume connected in parallel with said main chamber.

37. The apparatus as claimed in claim 21, wherein said means for applying said first positive pressure includes a positive pressure source including a main chamber, and said means for reducing the pressure at said second end of said conduit to said second positive pressure includes an auxiliary chamber having a fixed volume connected in series with said main chamber.

38. A medical apparatus, comprising an inflatable member having an inflated condition and a deflated condition;

a working gas for inflating said inflatable member;

a conduit having a first end connected to said inflatable member and a second end;

a main pressure source for supplying a first amount of said working gas to said second end of said conduit and for removing said first amount of said working gas from said second end of said conduit;

a positive pressure isolator connected in parallel with said main pressure source and having a primary side, a secondary side and a movable member separating said primary side from said secondary side, said secondary side being connected in flow communication with said second end of said conduit;

a positive pressure source for supplying a positive pressure to said primary side of said positive pressure isolator to move said movable member toward said secondary side of said positive pressure isolator, thereby moving a second amount of said working gas from said secondary side of said positive pressure isolator to said second end of said conduit; and a controller for controlling the supply of positive pressure to said positive pressure isolator;

whereby said inflatable member is placed in said inflated condition by supplying said first amount of said working gas from said main pressure source to said second end of said conduit together with movement of said second amount of said working gas from said secondary side of said positive pressure isolator to said second end of said conduit.

39. The medical apparatus as claimed in claim 38, wherein said main pressure source includes a main isolator having a primary side, a secondary side and a movable member separating said primary side from said secondary side, said secondary side being connected in flow communication with said second end of said conduit, a main positive pressure source for supplying a positive pressure to said primary side of said main isolator to move said movable member toward said secondary side of said main isolator, thereby moving said first amount of said working gas to said second end of said conduit, and a main negative pressure source for supplying a negative pressure to said primary side of said main isolator to move said movable member toward said primary side of said main isolator, thereby moving said first amount of said working gas from said second end of said conduit to said secondary side of said main isolator.

40. The medical apparatus as claimed in claim 38, further comprising a negative pressure isolator connected in parallel with said main pressure source and having a primary side, a secondary side and a movable member separating said primary side from said secondary side, said secondary side being connected in flow communication with said second end of said conduit;

a negative pressure source for supplying a negative pressure to said primary side of said negative pressure isolator to move said movable member toward said primary side of said negative pressure isolator, thereby moving a third amount of said working gas from said second end of said conduit to said secondary side of said negative pressure isolator; and a controller for controlling the supply of negative pressure to said negative pressure isolator;

whereby said inflatable member is placed in said deflated condition by removing said first amount of said working gas from said second end of said conduit to said main pressure source together with movement of said third amount of said working gas from said second end of said conduit to said secondary side of said negative pressure isolator.

* * * * *